US011013407B2

(12) United States Patent
Gonzalez et al.

(10) Patent No.: US 11,013,407 B2
(45) Date of Patent: May 25, 2021

(54) INTRAOCULAR PRESSURE MEASUREMENT FOR AN EYE DOCKED TO A LASER SYSTEM

(71) Applicant: AMO Development, LLC, Santa Ana, CA (US)

(72) Inventors: Javier G. Gonzalez, Palo Alto, CA (US); Michael Brett, San Jose, CA (US); Phillip Gooding, Mountain View, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

(21) Appl. No.: 16/278,035

(22) Filed: Feb. 15, 2019

(65) Prior Publication Data

US 2020/0260954 A1    Aug. 20, 2020

(51) Int. Cl.
| | | |
|---|---|---|
| *A61B 3/16* | (2006.01) | |
| *A61F 9/008* | (2006.01) | |
| *A61B 3/10* | (2006.01) | |
| *A61B 3/107* | (2006.01) | |
| *A61B 90/00* | (2016.01) | |

(52) U.S. Cl.
CPC ............. *A61B 3/16* (2013.01); *A61B 3/102* (2013.01); *A61B 3/107* (2013.01); *A61F 9/008* (2013.01); *A61B 2090/064* (2016.02); *A61F 2009/00842* (2013.01); *A61F 2009/00851* (2013.01); *A61F 2009/00855* (2013.01); *A61F 2009/00872* (2013.01)

(58) Field of Classification Search
CPC ........... A61B 3/16; A61B 3/102; A61B 3/107; A61B 2030/064; A61B 3/10–3/185; A61B 2090/064–2090/065; A61B 18/20–18/28; A61F 2009/00842; A61F 2009/00851; A61F 2009/00855; A61F 2009/00872; A61F 9/008–2009/00897
USPC ............................................. 606/4–6, 10–12
See application file for complete search history.

(56) References Cited

U.S. PATENT DOCUMENTS

| | | |
|---|---|---|
| 5,830,139 A | 11/1998 | Abreu |
| 6,440,070 B2 | 8/2002 | Israel |
| 7,935,058 B2 | 5/2011 | Dupps, Jr. et al. |

(Continued)

OTHER PUBLICATIONS

International Search Report and Written Opinion for Application No. PCTIB2020050876, dated Mar. 31, 2020, 7 pages.

*Primary Examiner* — Jonathan T Kuo
(74) *Attorney, Agent, or Firm* — Johnson & Johnson Surgical Vision, Inc.

(57) ABSTRACT

A method for measuring the intraocular pressure (IOP) of an eye docked to an ophthalmic surgical laser system via a patient interface assembly. While the eye is docked to the laser system, and as the vertical force exerted on the eye by the patient interface fluctuates as the patient breaths and moves, the amount of corneal deformation is continuously measured by an optical coherence tomography device of the laser system and the force exerted on the eye is continuously measured by force sensors integrated in the patient interface assembly. Based on the real-time force signal and real-time corneal deformation signal, a controller calculates a linear relationship between force and corneal deformation, and determines the IOP of the docked eye by comparing a slope of the linear relationship against a pre-established slope vs. IOP calibration curve. The IOP of the docked eye can be used when setting laser treatment parameters.

16 Claims, 4 Drawing Sheets

(56) References Cited

U.S. PATENT DOCUMENTS

| | | |
|---|---|---|
| 8,652,044 B2 | 2/2014 | Abramov |
| 2010/0152565 A1 | 6/2010 | Thomas et al. |
| 2011/0196350 A1 | 8/2011 | Friedman et al. |
| 2012/0277569 A1 | 11/2012 | Hogan |
| 2013/0085370 A1 | 4/2013 | Friedman et al. |
| 2013/0211285 A1 | 8/2013 | Fuller et al. |
| 2014/0128821 A1 | 5/2014 | Gooding et al. |
| 2014/0128852 A1 | 5/2014 | Gooding et al. |
| 2015/0031993 A1 | 1/2015 | Buckland et al. |
| 2015/0121997 A1 | 5/2015 | Lam et al. |
| 2015/0141972 A1 | 5/2015 | Woodley et al. |
| 2016/0106582 A1 | 4/2016 | Campos et al. |
| 2016/0374555 A1 | 12/2016 | Kontiola et al. |

INTRAOCULAR PRESSURE MEASUREMENT FOR AN EYE DOCKED TO A LASER SYSTEM

BACKGROUND OF THE INVENTION

Field of the Invention

This invention relates to ophthalmic laser surgery and diagnostics, and in particular, it relates to a method of measuring intraocular pressure while the patient's eye is docked to a surgical laser system.

Description of Related Art

Intraocular pressure (IOP), or the pressure inside the eye, ranges from 12-18 mmHg for a normal healthy eye. When a patient's eye is mechanically coupled to a patient interface device during laser ophthalmic surgery, the IOP can increase by 20 mmHg to 100 mmHg or even higher. Conventionally, IOP is measured with a tonometer. Various forms of tonometers are available. For example, Goldman tonometry, a widely used IOP measurement method, uses a special prism placed against the patient's cornea to apply an adjustable force, while the examiner makes various observations. Perkins tonometer is another type of applanation tonometer which is portable. A pneumatonometer measures IOP by blowing air against the cornea and measuring resistance from the cornea using a pneumatic sensor. A non-contact tonometry method (air-puff tonometry) directs air pulses to flatten the cornea while measuring corneal applanation using an electro-optical detector.

Some examples of tonometers and other systems of IOP measurement are described in U.S. Pat. Nos. 5,830,139 and 6,440,070, and U.S. Pat. Appl. Pub. Nos. 20100152565, and 20150121997.

Other examples of IOP measurement methods include:

U.S. Pat. No. 7,935,058, which describes systems and methods "for characterizing biomechanical properties of tissue within an eye. A perturbation component introduces a stress to the eye tissue. An imaging component is operative to obtain an image of the eye tissue. A first image of the tissue can be obtained prior to the introduction of the stress and a second image of the tissue can be obtained after the introduction of the stress. An image analysis component compares the first image and the second image as to determine at least one biomechanical property of the tissue." (Id., Abstract.)

U.S. Pat. Appl. Pub. No. 2012/0277569, which describes "a method, apparatus and system for measuring bio-medical attributes of the eye, such as internal or intraocular pressure. The invention enables taking measurements of the relative location of various surfaces of components of the eye under different conditions. The invention provides for applying a pressure disturbance to the eye acoustically and, using non-invasive optical techniques to perform measurements of vibrations or measurements of the time varying relative location of one or more surfaces or structures in a manner correlated with the pressure disturbance." (Id., Abstract.)

U.S. Pat. Appl. Pub. No. 2013/0085370, which describes a systems and methods for generating cross-linking activity in an eye, where "a feedback system monitors a biomechanical strength of the eye in response to the photoactivation of a cross-linking agent applied to an eye. The feedback system includes a perturbation system that applies a force to the eye and a characterization system that determines an effect of the force on the eye. The effect of the force provides an indicator of the biomechanical strength of the eye. The characterization system determines the effect of the force on the eye by measuring an amount of deformation caused by the force or a rate of recovery from the deformation." (Id., Abstract.) The perturbation system may apply intraocular pressure, acoustic or ultrasound pressure waves, shear supersonic ultrasound, or a laser light to the eye. (Id., para. [0010].)

U.S. Pat. Appl. Pub. No. 2015/0031993, which describes methods for performing a surgical procedure using optical coherence tomography (OCT). The method further includes managing intraocular pressure using OCT, by comparing a pre-surgical shape of a cornea to an intrasurgical or post-surgical shape of a cornea. (Id., para. [0024].)

SUMMARY

Most conventional IOP measurement methods measure the IOP of the eye when the eye is not mechanically coupled to a surgical laser system. Once the patient's eye is mechanically coupled to the laser system via the patient interface device (referred to as "docked"), most conventional methods are not able to accurately measure the TOP, which has changed from the normal values due to the mechanical coupling.

Accordingly, the present invention is directed to a method and related apparatus for TOP measurement that substantially obviates one or more of the problems due to limitations and disadvantages of the related art.

An object of the present invention is to provide a method and apparatus for measuring the IOP of a docked eye.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method of measuring intraocular pressure of an eye of a patient while the eye is docked to a surgical laser system via a patient interface assembly, which includes: using force sensors in the patient interface assembly, continuously measuring an external force exerted on the eye by the patient interface assembly and outputting a real-time external force signal to a controller of the surgical laser system; using an imaging device of the surgical laser system, continuously measuring a corneal deformation of the patient's docked eye and outputting a real-time corneal deformation signal to the controller; the controller calculating a parameter of a relationship between the real-time external force signal and the real-time corneal deformation signal; the controller determining the intraocular pressure of the docked eye based on the calculated parameter and a calibration curve between values of intraocular pressure and values of the parameter; and thereafter, the controller controlling the surgical laser system based in part on the determined intraocular pressure to perform treatment on the docked eye.

Preferably, the parameter is a slope of a linear relationship between the external force signal and the corneal deformation signal.

Preferably, the continuous measurement of the external force and the continuous measurement of the corneal deformation are performed without any adjustment of positions of the surgical laser system or a patient support bed on which the patient is situated.

In another aspect, the present invention provides an ophthalmic surgical laser system, which includes: a laser device configured to generate a laser beam; a laser beam delivery device configured to deliver the laser beam; a patient interface assembly, configured to be coupled to the laser beam delivery device at one end and coupled to a patient's eye at another end, the patient interface assembly including at least one force sensor for sensing a force exerted by the patient interface assembly on the eye and generate a real-time external force signal representing the exerted force; an imaging device configured to image structures of the eye that is coupled to the patient interface assembly and generate a real-time corneal deformation signal representing a deformation of a cornea of the eye; and a controller coupled to the laser device, the laser beam delivery device, the at least one force sensor and the imaging device, configured to: continuously receive the real-time external force signal and the corneal deformation signal; calculate a parameter of a relationship between the real-time external force signal and the real-time corneal deformation signal; determine an intraocular pressure of the eye that is coupled to the patient interface assembly based on the calculated parameter and a calibration curve between values of intraocular pressure and values of the parameter; and control the laser device and the laser beam delivery device based in part on the determined intraocular pressure to perform treatment on the eye.

In another aspect, the present invention provides a computer program product comprising a computer usable non-transitory medium (e.g. memory or storage device) having a computer readable program code embedded therein for controlling a data processing apparatus, the computer readable program code configured to cause the data processing apparatus to execute the above process.

It is to be understood that both the foregoing general description and the following detailed description are exemplary and explanatory and are intended to provide further explanation of the invention as claimed.

DETAILED DESCRIPTION OF PREFERRED EMBODIMENTS

Knowledge of the IOP while a patient's eye is docked to the surgical laser system is helpful for laser treatment of the eye. For example, in a laser procedure that forms an arcuate incision in the patient's cornea to correct astigmatism, an accurately measured IOP of the docked eye may be used as a parameter in a nomogram that can be used to predict corneal curvature relaxation as a function of the shape of the arcuate incision. The IOP of the docked eye may also be used to contrast against the regular IOP of undocked eye for other applications.

Embodiments of the present invention provide a method that utilizes sensors and detectors of the ophthalmic surgical laser system to measure the patient's IOP while the eye is docked to the laser system via a patient interface assembly. More specifically, the IOP of the docked eye is measured by using force sensors that are integrated into the patient interface assembly, and using an optical imaging system of the surgical laser system such as an optical coherence tomography (OCT) system to measure the corneal shape.

Figure 1:
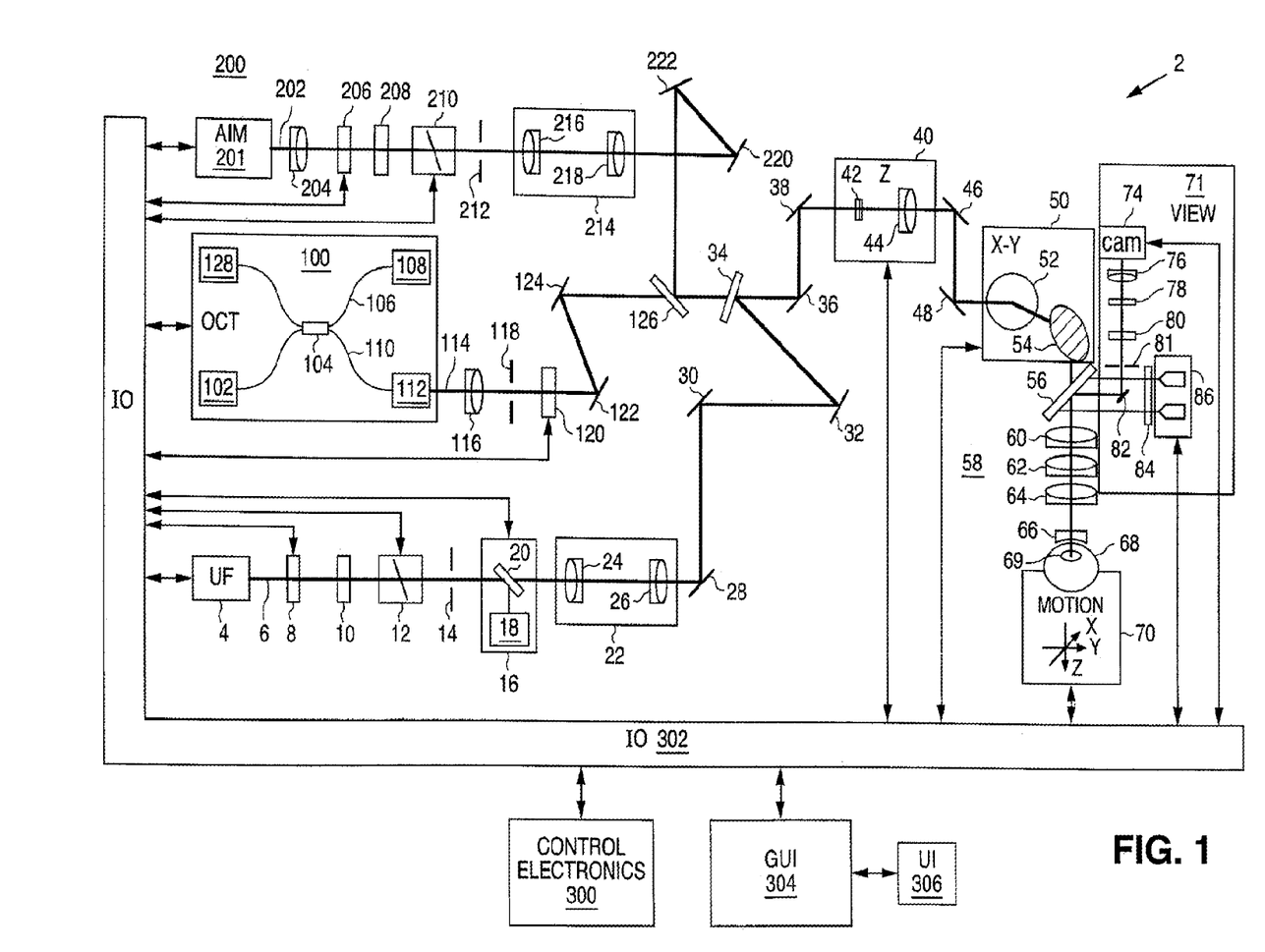
FIG. 1 is a schematic diagram of an ophthalmic surgical laser system in which embodiments of the present invention may be implemented.

The present invention can be implemented by a laser system that projects or scans an optical beam into a patient's eye 68, such as system 2 shown in FIG. 1 which includes an ultrafast (UF) light source 4 (e.g. a femtosecond laser). Using this system, a beam may be scanned in a patient's eye in three dimensions: X, Y, Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser 4 may be a repetitively pulsed 1035 nm device that produces 500 fs pulses at a repetition rate of 100 kHz and an individual pulse energy in the ten microjoule range.

The laser 4 is controlled by control electronics 300, via an input and output device 302, to create optical beam 6. Control electronics 300 may be a computer, microcontroller, etc., including a memory storing computer executable programs and a processor configured to execute the programs. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated UF light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the UF beam 6. Additionally, the orientation of linear polarizer 10 determines the incident polarization state incident upon beamcombiner 34, thereby optimizing beamcombiner throughput.

The UF beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light.

After exiting conditioning stage 22, beam 6 reflects off of fold mirrors 28, 30, & 32. These mirrors can be adjustable for alignment purposes. The beam 6 is then incident upon beam combiner 34. Beamcombiner 34 reflects the UF beam 6 (and transmits both the OCT 114 and aim 202 beams described below). For efficient beamcombiner operation, the angle of incidence is preferably kept below 45 degrees and the polarization where possible of the beams is fixed. For the UF beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40.

After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of UF focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An f-theta lens 58 of focal length 60 mm generating a spot size of 10 µm, over a field of 10 mm, with an input beam size of 15 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the optical beam 6 into the patient's eye 68 while helping to stabilize eye position. The positioning and character of optical beam 6 and/or the scan pattern the beam 6 forms on the eye 68 may be further controlled by use of an input device such as a joystick, or any other appropriate user input device (e.g. GUI 304) to position the patient and/or the optical system.

The UF laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 1, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information may then be loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs either time domain, frequency or single point detection techniques. In FIG. 1, a frequency domain technique is used with an OCT wavelength of 920 nm and bandwidth of 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the UF beam 6 in the focal plane and therefore the OCT beam 114 is smaller in diameter than the UF beam 6 at the beamcombiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beamcombiners 126 & 34. Mirrors 122 & 124 may be adjustable for alignment purposes and in particular for overlaying of OCT beam 114 to UF beam 6 subsequent to beamcombiner 34. Similarly, beamcombiner 126 is used to combine the OCT beam 114 with the aim beam 202 described below.

Once combined with the UF beam 6 subsequent to beamcombiner 34, OCT beam 114 follows the same path as UF beam 6 through the rest of the system. In this way, OCT beam 114 is indicative of the location of UF beam 6. OCT beam 114 passes through the z-scan 40 and x-y scan 50 devices then the objective lens 58, contact lens 66 and on into the eye 68. Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y Z of UF beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference atm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by a an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 6 in the focal plane and therefore aim beam 202 is of similar diameter to the UF beam at the beamcombiner 34 location. Because the aim beam is meant to stand-in for the UF beam 6 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beamcombiners 126 and 34, thereby fixing the polarization state and allowing for optimization of the beamcombiners' throughput. Of course, if a semiconductor laser is used as aim beam light source 200, the drive current can be varied to adjust the optical power.

The aim beam 202 proceeds through a shutter 210 and aperture 212. The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

The aim beam 202 next passes through a beam conditioning device 214. Beam parameters such as beam diameter, divergence, circularity, and astigmatism can be modified using one or more well known beaming conditioning optical elements. In the case of an aim beam 202 emerging from an optical fiber, the beam conditioning device 214 can simply include a beam expanding telescope with two optical elements 216 and 218 in order to achieve the intended beam size and collimation. The final factors used to determine the aim beam parameters such as degree of collimation are dictated by what is necessary to match the UF beam 6 and aim beam 202 at the location of the eye 68. Chromatic differences can be taken into account by appropriate adjustments of beam conditioning device 214. In addition, the optical system 214 is used to image aperture 212 to a desired location such as a conjugate location of aperture 14.

The aim beam 202 next reflects off of fold mirrors 222 & 220, which are preferably adjustable for alignment registration to UF beam 6 subsequent to beam combiner 34. The aim beam 202 is then incident upon beam combiner 126 where the aim beam 202 is combined with OCT beam 114. Beamcombiner 126 reflects the aim beam 202 and transmits the OCT beam 114, which allows for efficient operation of the beamcombining functions at both wavelength ranges. Alternatively, the transmit and reflect functions of beamcombiner 126 can be reversed and the configuration inverted. Subsequent to beamcombiner 126, aim beam 202 along with OCT beam 114 is combined with UF beam 6 by beamcombiner 34.

A device for imaging the target tissue on or within the eye 68 is shown schematically in FIG. 1 as imaging system 71. Imaging system includes a camera 74 and an illumination light source 86 for creating an image of the target tissue. The imaging system 71 gathers images which may be used by the system controller 300 for providing pattern centering about or within a predefined structure. The illumination light source 86 for the viewing is generally broadband and incoherent. For example, light source 86 can include multiple LEDs as shown. The wavelength of the viewing light source 86 is preferably in the range of 700 nm to 750 nm, but can be anything that is accommodated by the beamcombiner 56, which combines the viewing light with the beam path for UF beam 6 and aim beam 202 (beamcombiner 56 reflects the viewing wavelengths while transmitting the OCT and UF wavelengths). The beamcombiner 56 may partially transmit the aim wavelength so that the aim beam 202 can be visible to the viewing camera 74. Optional polarization element 84 in front of light source 86 can be a linear polarizer, a quarter wave plate, a half-wave plate or any combination, and is used to optimize signal. A false color image as generated by the near infrared wavelength is acceptable.

The illumination light from light source 86 is directed down towards the eye using the same objective lens 58 and contact lens 66 as the UF and aim beam 6, 202. The light reflected and scattered off of various structures in the eye 68 are collected by the same lenses 58 & 66 and directed back towards beamcombiner 56. There, the return light is directed back into the viewing path via beam combiner and mirror 82, and on to camera 74. Camera 74 can be, for example but not limited to, any silicon based detector array of the appropriately sized format. Video lens 76 forms an image onto the camera's detector array while optical elements 80 & 78 provide polarization control and wavelength filtering respectively. Aperture or iris 81 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 71.

Coarse adjust registration is usually needed so that when the contact lens 66 comes into contact with the cornea, the targeted structures are in the capture range of the X, Y scan of the system. Therefore a docking procedure is preferred, which preferably takes in account patient motion as the system approaches the contact condition (i.e. contact between the patient's eye 68 and the contact lens 66. The viewing system 71 is configured so that the depth of focus is large enough such that the patient's eye 68 and other salient features may be seen before the contact lens 66 makes contact with eye 68.

Preferably, a motion control system 70 is integrated into the overall control system 2, and may move the patient, the system 2 or elements thereof, or both, to achieve accurate and reliable contact between contact lens 66 and eye 68. Furthermore, a vacuum suction subsystem and flange may be incorporated into system 2, and used to stabilize eye 68. The alignment of eye 68 to system 2 via contact lens 66 may be accomplished while monitoring the output of imaging system 71, and performed manually or automatically by analyzing the images produced by imaging system 71 electronically by means of control electronics 300 via IO 302. Force and/or pressure sensor feedback may also be used to discern contact, as well as to initiate the vacuum subsystem.

Alternative structures of a laser system useful in embodiments of the present invention are described in U.S. Pat. Appl. Pub. Nos. 2011/0196350 and 2015/0141972, the disclosures of which are incorporated herein by reference in their entireties.

In the laser system described above, the lens 66 of the patient interface is referred to as a contact lens as it can be used to contact the surface of the eye to stabilize eye position. To implement embodiments of the present invention, a patient interface using a non-contact lens is employed, as described below with reference to FIGS. 2A-2C and 3.

Figure 2A:
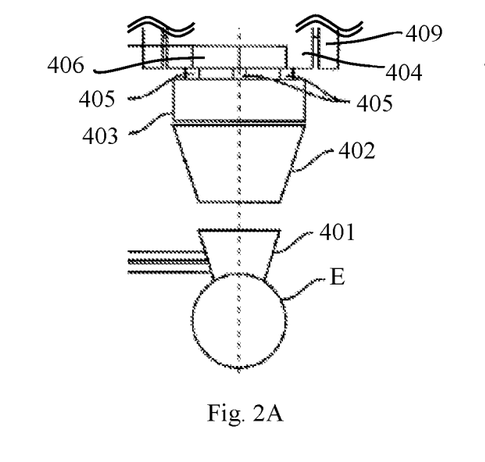
FIGS. 2A-2C and 3 schematically illustrate a patient interface assembly that may be used to implement an IOP measurement method according to embodiments of the present invention.
Figure 2B:
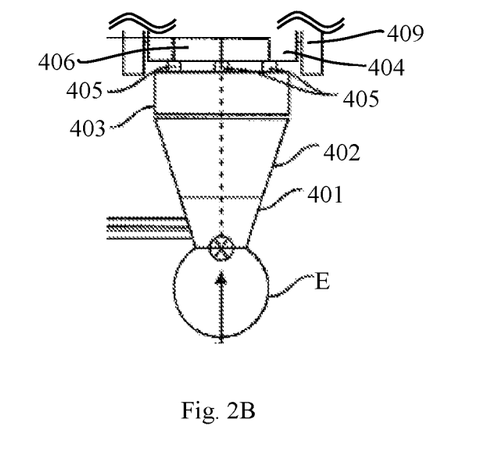

FIGS. 2A and 2B schematically illustrate a patient interface assembly and a process of coupling the patient's eye E to the surgical laser system via the patient interface assembly. The patient interface assembly includes a suction cup 401 which may include an annular vacuum ring (not shown in FIGS. 2A and 2B) for coupling to the eye with suction, a disposable lens cone 402 for coupling to the suction cup 401, and a coupler 403 for coupling the lens cone 402 to a main body 404 of the patient interface assembly. The main body is mounted on the housing 409 of a laser delivery head of the laser system, and may be movable in the vertical direction (i.e. the direction parallel to the optical axis of the objective lens of the laser system) relative to the housing.

As shown in FIG. 2B, once the suction cup 401 is coupled to the patient's eye and the disposable lens cone 402 is coupled to the coupler 403, the suction cup can be coupled to the disposable lens cone to accomplish docking of the eye to the laser system. During docking, the suction cup 401 (on the patient's eye) and the lens cone 402 can be moved toward each other by moving the laser delivery head and/or moving the patient support bed on which the patient lies.

Figure 2C:
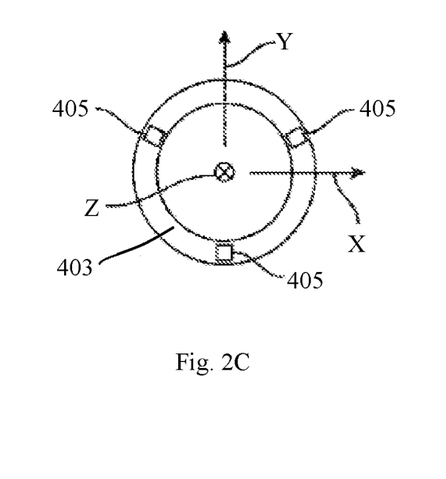

As shown in FIGS. 2A-2C, the patient interface assembly further includes a plurality of force sensors 405 disposed between and in physical contact with the main body 404 and the coupler 403. Preferably, the force sensors 405 lie in a horizontal plane normal to the vertical axis of the patient interface assembly (see FIG. 2C, top view of the coupler 403). In the example illustrated FIG. 2C, the force sensors 405 are positioned equidistant from a central vertical axis Z of the patient interface assembly and are equidistant from one another as well. The force sensors 405 measure the forces between the patient interface main body 404 and the coupler 403 along the vertical axis Z. The force differentials between the different force sensors 405 may be used to calculate the lateral forces between the main body 404 and the coupler 403, i.e., the X-direction and the Y-direction forces. When the suction cup 401 is coupled to both the eye and the lens cone 402, the force measured by the force sensors is an indication of the force between the patient interface assembly and the patient's eye.

In alternative embodiments, the force sensors may be located between other individual components of the patient interface assembly, such as between the lens code 402 and the coupler 403. The force sensors 405 may be piezoelectric sensors or other suitable sensors. The data regarding the measured forces is transmitted via a communications device 406 to the other subsystems of the laser system including, e.g., the control electronics, the GUI, and/or the user interface devices.

In the patient interface assembly, the space enclosed by the suction cup 401 above the eye's surface is filled with a suitable fluid to act as an optical medium between the optical lens and the cornea, so that the optical lens of the lens cone 402 does not directly contact the eye's surface when docked. An example of the suction cup 401 and lens cone 402 is illustrated in more detail in FIG. 3.

Figure 3:
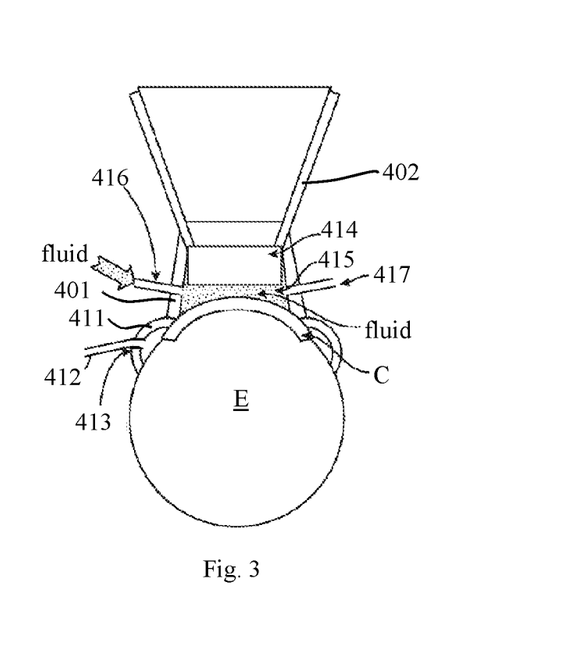

As shown in FIG. 3, the distal end of the suction cup 401 includes a suction ring 411 with an annular suction channel for coupling with the surface of the eye E using a vacuum force. The lens cone 402 includes an optically transmissive lens 414. During docking, the suction ring 411 is first placed in contact with the cornea C of the eye E to close the suction channel, and a vacuum is drawn through a suction line 412 which extends from a suction port 413 of the suction ring 411 to a vacuum source (not shown). This suction force secures the eye to the suction cut 401. The suction cup 401 and the lens cone 402 are then coupled to each other, where the distal surface of the lens 414 remains spaced vertically from the anterior surface of the cornea C, forming a chamber 415 in between. A suitable fluid can be filled in the chamber 415, via a fluid input port 416 and a fluid output port 417 on the suction cup 401, to acts as an optical medium between the cornea and the lens 414.

Further details of patient interface assemblies that may be used in embodiments of the present invention are described in U.S. Pat. Appl. Pub. Nos. 2014/0128852 and 2016/0106582, the disclosures of which are incorporated herein by reference in their entireties.

As indicated earlier, embodiments of the present invention provide a method of measuring the IOP of a docked eye using force sensors of the patient interface assembly and the OCT imaging system. This measurement method is based on the recognition by the inventors that when the eye is docked to the patient interface assembly and a force is exerted by the patient interface assembly against the eye, the corneal surface assumes a shape that is dependent on the IOP of the eye. Thus, the corneal shape measured using the OCT device of the laser system and the force measured by the force sensors of the patient interface assembly can be used together to calculate the IOP of the docked eye.

Figure 4A:
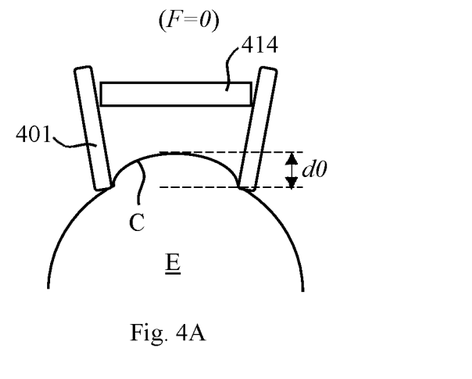
FIGS. 4A and 4B schematically illustrate a corneal deformation effect caused by an external force exerted by the patient interface assembly.
Figure 4B:
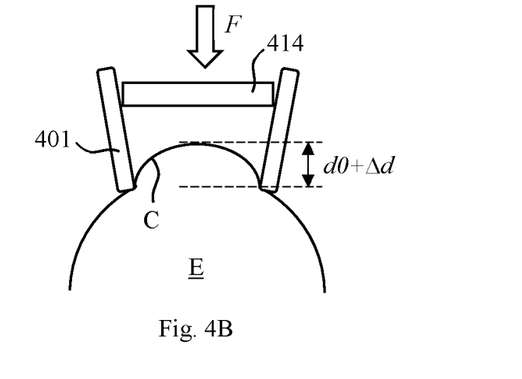

More specifically, the amount of corneal deformation induced by a given amount of external force exerted on the eye by patient interface assembly is dependent on the IOP of the eye. This effect is schematically illustrated in FIGS. 4A and 4B. In these illustrations, the eye E is docketed to the patient interface assembly, where only the suction cup 401 and the lens 414 of the lens cone are shown. Other parts of the patient interface assembly such as the suction ring, lens cone, etc. are not illustrated here; it should be understood that the part of the suction cup 401 that contacts the eye is the suction ring 411 as shown in FIG. 3.

As schematically illustrated in FIG. 4A, when the net vertical force exerted by the patient interface assembly on the eye is zero, the cornea protrudes upwards by a distance $d=d0$ at the corneal center (apex), relative to the distal end of the suction cup 401 where the suction ring makes contact against the eye's surface (the sclera). When a non-zero downward force is exerted on the eye by the patient interface assembly, the cornea will protrude upwards by a larger amount, as shown in FIG. 4B, where the corneal center is shown at a distance $d=d0+\Delta d$ relative to the distal end of the suction cup. In the latter situation, when a downward force is exerted, the eye deforms under the suction ring, locally sinking, and pushing the cornea to extend farther upwards. This is because the fluid inside the eye is essentially incompressible; thus, the fluid displaced by the sinking portion of the sclera under the suction ring pushes the cornea upward.

The larger the downward force, the larger the corneal deformation. Within the range of forces typically exerted by the patient interface assembly during an ophthalmic procedure, the relationship between the corneal deformation d and the external force F is approximately a linear relationship.

Figure 5:
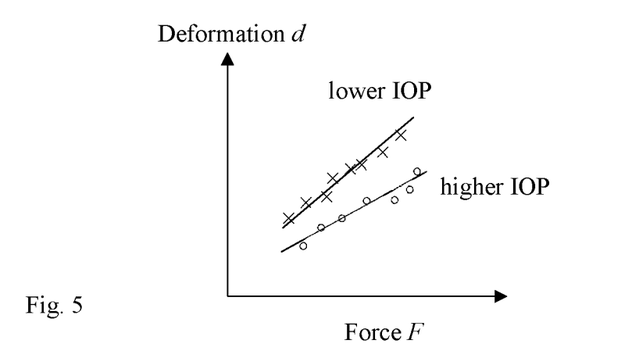
FIG. 5 schematically illustrates the effect of IOP on the linear relationship between the corneal deformation and the external force.

The relationship between corneal deformation d and external force F is affected by the IOP of the docked eye. This is because when the IOP is higher, i.e. the ocular surface tension is higher, the amount of corneal deformation caused by the same amount of external force will be less. Thus, the slope of the linear relationship between the deformation d and the force F is indicative of the IOP of the eye, where a smaller slope $\Delta d/\Delta F$ indicates a higher IOP. This effect is schematically illustrated in FIG. 5. Note that FIG. 5 does not represent actual experimental data; it is only intended to illustrate the principle of the IOP measurement method.

Note that in FIGS. 4A and 4B, the amount of corneal deformation d is defined relative to the distal end of the suction cup 401; alternatively, the deformation d can be defined relative to any pre-defined reference position, such as an internal reference position of the OCT system, the distal surface of the lens 414, etc. The choice of the reference position will not change the absolute value of the slope of the linear relationship between corneal deformation and external force, although it may change the sign of the slope.

When the patient's eye is docked to the laser system, the patient tends to move slightly under the laser system, caused by the patient's breathing, coughing, or other random motions. As a result, the vertical force exerted by the patient interface assembly on the eye changes with time as the patient moves. The IOP measurement method according to one embodiment takes advantage of this phenomenon to collect data points of external force F and corresponding corneal deformation d and use them to calculate the IOP.

Figure 6:
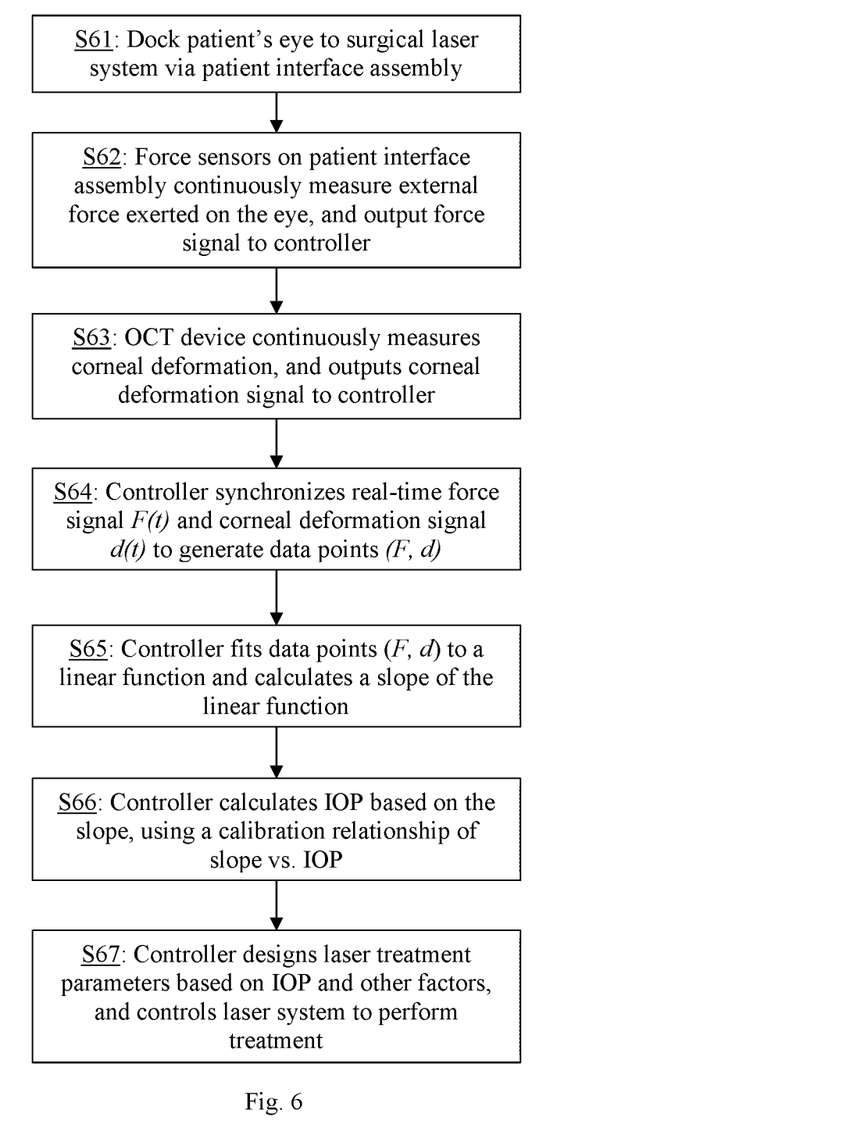
FIG. 6 schematically illustrates a method of measuring the IOP of a patient's eye while the eye is docked to the laser system according to an embodiment of the present invention.

A method of measuring the IOP of a patient's docked eye is described below with reference to FIG. 6. First, the eye is docked to the surgical laser system via the patient interface assembly (step S61). As described earlier, the patient interface assembly includes a number of force sensors configured to sense a vertical force exerted by the patient interface assembly on the patient's eye. Before laser treatment begins, the force sensors continuously measure the vertical external force exerted on the eye and outputs the force signal to a controller of the laser system (step S62). Meanwhile, the OCT device of the laser system is operated to continuously measure an amount of corneal deformation, and output the corneal deformation signal to the controller (step S63). In one embodiment, the OCT outputs a distance between the apex of the anterior corneal surface and the distal surface (or an apex of the distal surface if it is curved) of the lens of the patient interface assembly as the corneal deformation signal.

The measurements of the external force and corneal deformation (steps S62 and S63) are taken as the patient moves slightly in a natural and essentially random manner under the laser system due to the patient's breathing and other motions. Preferably, during this process, while the external force changes due to patient movements, no deliberate adjustment is made to the mechanical coupling of the eye to the patient interface assembly, either by the laser system or by the patient support bed. For example, the laser system and the patient support bed are not operated to compensate for any observed change of external force exerted on the eye, nor operated to deliberately exert a greater or lesser force on the eye; further, no other mechanical signals is deliberately applied to the eye to cause an mechanical impact on or inside the eye. Instead, the laser system merely measures the external force and the corneal deformation, in real time, as the changes naturally occur. This measurement may last, for example, for a minute or so or until sufficient data is gathered.

The controller synchronizes the received real-time external force signal F(t) and corneal deformation signal d(t) to generate multiple data points, each data point (F, d) being a pair of external force value F and corneal deformation value d at the same time point t (step S64). Once a sufficient amount of data is gathered, the controller fits the data points (F, d) to a linear function and calculates a slope of the linear function (step S65). The slope calculated in step S65 is compared to a calibration curve between the slope of the linear function and the IOP to determine the IOP of the patient's docked eye (step S66).

After the IOP of the docked eye is measured, laser treatment can be performed on the docked eye (step S67). For example, the laser treatment may include forming an arcuate incision on the cornea to correct astigmatism. In this step, the measured IOP is used as one of the factors to be considered when designing the laser treatment parameters. For example, when designing the shape of the arcuate incision to be formed, the IOP and other factors are considered, include the amount of astigmatism correction to be achieved, the shape of the cornea, other biomechanical properties of the eye, etc. In one embodiment, the IOP is used as a parameter in a nomogram that is used to predict corneal curvature relaxation as a function of the shape of the arcuate incision.

In the above-described IOP measurement method, the calibration curve of slope vs. TOP is established beforehand through experiments conducted on multiple eyes with different IOPs. More specifically, in the calibration experiments, for each eye, steps S61 to S65 are performed to dock the eye and measure the slope of the linear relationship between the external force and corneal deformation, and the IOP of the docked eye is measured using an independent method.

In one embodiment, the independent measurement of IOP of the docked eye is performed as follows. The eye is mechanically coupled to the suction cup 401 of the patient interface assembly via the vacuum force in the suction ring 411, but the suction cup 401 is not coupled to the lens cone 402, and the space 415 above the eye is not filled with a fluid. In this state, the TOP is approximately the same as the IOP when the eye is fully docked to the laser system via the patient interface assembly, as the change of IOP induced by docking is primarily caused by the mechanical coupling of the suction cup 401 to the eye. A suitable tonometer is then used to measure the IOP through the free space above the eye.

As seen from the above descriptions, the method of measuring IOP of a docked eye is based on signals generated by the OCT device and the force sensors of the surgical laser system. These components are existing components of many surgical laser system and are used to perform other functions. For example, the OCT system can be used to image various tissues of the eye and measure positions of these tissues, which is critical for laser treatment. The force sensors can be used, for example, to provide feedback signals to control a laser delivery head (a floating head) of the laser system and/or the patient support bed to counteract patient movements during laser treatment; to provide feedback signals for the laser system to offset the position of the laser beam to increase accuracy of the placement of the beam in the eye in response to patient movements; to monitor movements of the eye during treatment, and use it in combination with other monitoring devices to predict an imminent vacuum loss event; etc. Thus, for a surgical laser system that already incorporates the OCT system and the force sensors, the IOP measurement described above does not require additional hardware components in the laser system. This provides a significant advantage over many other IOP measurement devices.

In one aspect, the present invention provides a process of operating an ophthalmic laser system. In another aspect, the present invention provides an ophthalmic laser system having, inter alia, a controller that is configured to control the ophthalmic laser system to perform the process. In another aspect, the present invention provides a computer program product comprising a computer usable non-transitory medium (e.g. memory or storage device) having a computer readable program code embedded therein, the computer readable program code being configured to cause the ophthalmic laser system to perform the process.

It will be apparent to those skilled in the art that various modification and variations can be made in the IOP measurement method and related apparatus of the present invention without departing from the spirit or scope of the invention. Thus, it is intended that the present invention cover modifications and variations that come within the scope of the appended claims and their equivalents.

What is claimed is:

1. A method of measuring intraocular pressure of an eye of a patient while the eye is docked to a surgical laser system via a patient interface assembly, the method comprising:
   using force sensors in the patient interface assembly, continuously measuring an external force exerted on the eye by the patient interface assembly and outputting a real-time external force signal to a controller of the surgical laser system;
   using an imaging device of the surgical laser system, continuously measuring a corneal deformation of the patient's docked eye and outputting a real-time corneal deformation signal to the controller;
   the controller calculating a parameter of a relationship between the real-time external force signal and the real-time corneal deformation signal;
   the controller determining the intraocular pressure of the docked eye based on the calculated parameter and a calibration curve between values of intraocular pressure and values of the parameter; and
   thereafter, the controller controlling the surgical laser system based in part on the determined intraocular pressure to perform treatment on the docked eye.

2. The method of claim 1, wherein the continuous measurement of the external force and the continuous measurement of the corneal deformation are performed without any adjustment of positions of the surgical laser system or a patient support bed on which the patient is situated.

3. The method of claim 1, wherein the corneal deformation is a distance between an apex of an anterior corneal surface of the eye and a reference location of the patient interface assembly.

4. The method of claim 3, wherein the parameter is a slope of a linear relationship between the external force signal and the corneal deformation signal.

5. The method of claim 3, wherein the step of the controller calculating the parameter includes:
   synchronizing the external force signal and the corneal deformation signal to obtain a plurality of data points, each data point being a pair of external force value and corneal deformation value at a same time point;
   fitting the plurality of data points to a linear function; and
   calculating a slope of the linear function.

6. The method of claim 1, wherein the imaging device of the surgical laser system is an optical coherence tomography device.

7. The method of claim 1, wherein the step of the controller controlling the surgical laser system based in part on the determined intraocular pressure to perform treatment on the docked eye includes:
   based in part on the intraocular pressure, calculating laser treatment parameters for performing an incision on the eye; and
   controlling the laser system to deliver a laser beam into the eye according to the laser treatment parameters to form the incision.

8. The method of claim 7, wherein the incision is an arcuate incision formed in a cornea of the eye and the laser treatment parameters define a shape of the arcuate incision.

9. An ophthalmic surgical laser system, comprising:
   a laser device configured to generate a laser beam;
   a laser beam delivery device configured to deliver the laser beam;
   a patient interface assembly, configured to be coupled to the laser beam delivery device at one end and coupled to a patient's eye at another end, the patient interface assembly including at least one force sensor for sensing a force exerted by the patient interface assembly on the eye and generate a real-time external force signal representing the exerted force;
   an imaging device configured to image structures of the eye that is coupled to the patient interface assembly and generate a real-time corneal deformation signal representing a deformation of a cornea of the eye; and
   a controller coupled to the laser device, the laser beam delivery device, the at least one force sensor and the imaging device, configured to:
      continuously receive the real-time external force signal and the corneal deformation signal;
      calculate a parameter of a relationship between the real-time external force signal and the real-time corneal deformation signal;
      determine an intraocular pressure of the eye that is coupled to the patient interface assembly based on the calculated parameter and a calibration curve between values of intraocular pressure and values of the parameter; and
      control the laser device and the laser beam delivery device based in part on the determined intraocular pressure to perform treatment on the eye.

10. The laser system of claim 9, further comprising a patient support bed configured to accommodate the patient, the patient support bed being coupled to the controller;
    wherein controller is configured to continuously receives the external force signal and the corneal deformation signal without changing positions of the laser beam delivery device or the patient support bed.

11. The laser system of claim 9, wherein the corneal deformation is a distance between an apex of an anterior corneal surface of the eye and a reference location of the patient interface assembly.

12. The laser system of claim 11, wherein the parameter is a slope of a linear relationship between the external force signal and the corneal deformation signal.

13. The laser system of claim 11, wherein the controller is configured to calculate the parameter by:
    synchronizing the external force signal and the corneal deformation signal to obtain a plurality of data points, each data point being a pair of external force value and corneal deformation value at a same time point;
    fitting the plurality of data points to a linear function; and
    calculating a slope of the linear function.

14. The laser system of claim 9, wherein the imaging device is an optical coherence tomography device.

15. The laser system of claim 9, wherein the controller is configured to control the laser device and the laser beam delivery device by:
    based in part on the intraocular pressure, calculating laser treatment parameters for performing an incision on the eye; and
    controlling the laser device and the laser beam delivery device to deliver a laser beam into the eye according to the laser treatment parameters to form the incision.

16. The laser system of claim 15, wherein the incision is an arcuate incision formed in a cornea of the eye and the laser treatment parameters define a shape of the arcuate incision.

* * * * *